United States Patent
Johnson

(10) Patent No.: US 10,297,135 B1
(45) Date of Patent: May 21, 2019

(54) DRYNESS SENSOR

(71) Applicant: Perfection Holdings LLC, Holt, MO (US)

(72) Inventor: Matthew T. Johnson, Holt, MO (US)

(73) Assignee: Perfection Holdings LLC, Holt, MO (US)

( * ) Notice: Subject to any disclaimer, the term of this patent is extended or adjusted under 35 U.S.C. 154(b) by 0 days.

(21) Appl. No.: 15/952,969

(22) Filed: Apr. 13, 2018

(51) Int. Cl.
*G01N 19/10* (2006.01)
*G08B 21/20* (2006.01)
*B01J 20/22* (2006.01)

(52) U.S. Cl.
CPC .......... *G08B 21/20* (2013.01); *B01J 20/22* (2013.01); *G01N 19/10* (2013.01)

(58) Field of Classification Search
CPC ....... A01G 25/167; H01H 35/42; G01W 1/14; G01N 19/10
See application file for complete search history.

(56) References Cited

U.S. PATENT DOCUMENTS

| | | | | |
|---|---|---|---|---|
| 4,246,575 A * | 1/1981 | Purtell | ................... | H01H 35/42 200/61.04 |
| 5,329,081 A * | 7/1994 | Jones | ................... | A01G 25/167 200/61.04 |
| 6,570,109 B2 | 5/2003 | Klinefelter et al. | | |
| 6,977,351 B1 | 12/2005 | Woytowitz | | |
| 7,949,433 B2 | 5/2011 | Hem et al. | | |
| 2009/0271044 A1 * | 10/2009 | Bangalore | ............... | G01W 1/14 700/284 |
| 2014/0360253 A1 * | 12/2014 | Gibson | .................. | G01N 19/10 73/73 |

OTHER PUBLICATIONS

Wikipedia, Expandable water toy, printed Jul. 3, 2017.
Wikipedia, Superabsorbent polymer, printed Jul. 3, 2017.
M2 Polymer Technologies, Inc., SAP Cubes, printed from http://www.m2polymer.com/html/sap-cubes.html on Jul. 3, 2017.
Rain Bird, RSD Series Rain Sensor, 2012.
Wikipedia, Soil mosture sensor, printed Aug. 3, 2017.
SparkFun, SparkFun Soil Moisture Sensor, printed from https://www.sparkfun.com/products/13322 on Aug. 3, 2017.

(Continued)

*Primary Examiner* — Hongmin Fan
(74) *Attorney, Agent, or Firm* — Martin & Associates, LLC; Derek P. Martin

(57) ABSTRACT

A dryness sensor uses a block of superabsorbent polymer that absorbs liquid and increases in size as liquid is absorbed. When the block of superabsorbent polymer increases in size in the presence of liquid, the block of superabsorbent polymer contacts one or more electronic components coupled to a moisture detection circuit that provides an indication of moisture. When the block of superabsorbent polymer loses moisture, it decreases in size until the block of superabsorbent polymer no longer contacts the one or more electronic components. The moisture detection circuit detects when the block of superabsorbent polymer no longer contacts the one or more electronic components, and provides an alert indicating a lack of moisture. The dryness sensor could be used, for example, to monitor the moisture content of soil in a pot that has a house plant growing in the pot.

17 Claims, 10 Drawing Sheets

(56) References Cited

OTHER PUBLICATIONS

Toro, Wireless & Wired RainSensor, 2014.
wemakethings.net, "Chirp!—the plant watering alarm", printed from httpsL//wemakethings.net/chirp/ on Aug. 3, 2017.
Meeks et al., Long Term Expanding-Disk Rain Sensor Accuracy, Journal of Irrigation and Drainage Engineering, 2012.138:16-20, Jan. 2012.
sprinklerwarehouse.com, Different Types of Rain Sensors for Irrigation Controllers, printed from www. sprinklerwarehouse.com/rain-sensor-types-s/8309.html on Sep. 14, 2017.

\* cited by examiner

DRYNESS SENSOR

BACKGROUND

1. Technical Field

This disclosure generally relates to watering plants, and more specifically relates to a dryness sensor that can be used as part of a system for watering plants.

2. Background Art

The health of plants depends on many factors, including how much water the plant receives, and the proper space of time between watering. Many different systems have been developed over the years for watering plants. For example, sprinkler systems have been developed for watering grass, while drip irrigation systems are often used for individual trees or plants. Most known watering systems are manual, which require a person to turn on the water to the watering system, then manually turn off the water later when the person believes the plants have received enough water. Other known watering systems are timed and turn on at set periodic intervals. For example, a residential system for watering the lawn and bushes at a person's house can be set to turn on every other day for a half hour. Both manual and timed watering systems typically do not take into account whether or not the plant actually needs water. For example, in the timed residential system referenced above, if a rain storm waters the grass during the night before the system is set to turn on, the timed system will still turn on and water the grass, even though the grass does not need watering due to the rain storm.

The problem with using manual or timed systems discussed above can be somewhat mitigated by incorporating one or more moisture sensors that measure the moisture in the soil, then turn on the watering system only when the soil needs moisture. Thus, in the example given above with a rain storm occurring during the night that waters a lawn, when the time comes for the watering system to turn on automatically the next morning, the watering system will not be turned on if the reading from one or more moisture sensor indicates the lawn does not need to be watered.

Many different systems have been developed over the years for monitoring moisture in soil. Some farmers use moisture sensors that indicate the moisture level of the soil, which information the farmer can use to adjust the irrigation schedule for the farmer's crops. Other moistures sensors have been developed for house plants. One known moisture sensor called Chirp can be installed near a plant and emits a tiny chirp when the soil is dry, indicating the plant needs to be watered. The alarm level for the Chirp can be set for each plant individually.

Known moisture sensors typically include electronics that can precisely measure the moisture content of the soil, sometimes in increments of less than 1%. This type of sophisticated moisture measurement is not needed in determining the water needs of most plants, including houseplants.

Most people water houseplants periodically. Many people tend to over-water houseplants, which can make the houseplants less healthy. Some people go for long periods of time between waterings, which can result in the soil in the pot contracting away from the sides of the pot. When this occurs, once the person waters the plant again, there is a nearly direct route for water to flow past the soil into the catch basin on the pot, instead of being soaked up by the soil.

What is needed is a way to water plants that overcomes the disadvantages discussed above.

BRIEF SUMMARY

A dryness sensor uses a block of superabsorbent polymer that absorbs liquid and increases in size as liquid is absorbed. When the block of superabsorbent polymer increases in size in the presence of liquid, the block of superabsorbent polymer contacts one or more electronic components coupled to a moisture detection circuit that provides an indication of moisture. When the block of superabsorbent polymer loses moisture, it decreases in size until the block of superabsorbent polymer no longer contacts the one or more electronic components. The moisture detection circuit detects when the block of superabsorbent polymer no longer contacts the one or more electronic components, and provides an alert indicating a lack of moisture. The alert can include a visual alert, an audio alert, and an electronic message. The dryness sensor could be used, for example, to monitor the moisture content of soil in a pot that has a house plant growing in the pot.

The foregoing and other features and advantages will be apparent from the following more particular description, as illustrated in the accompanying drawings.

BRIEF DESCRIPTION OF THE SEVERAL VIEWS OF THE DRAWING(S)

The disclosure will be described in conjunction with the appended drawings, where like designations denote like elements, and:

DETAILED DESCRIPTION

A dryness sensor uses a block of superabsorbent polymer that absorbs liquid and increases in size as liquid is absorbed. When the block of superabsorbent polymer increases in size in the presence of liquid, the block of superabsorbent polymer contacts one or more electronic components coupled to a moisture detection circuit that provides an indication of moisture. When the block of superabsorbent polymer loses moisture, it decreases in size until the block of superabsorbent polymer no longer contacts the one or more electronic components. The moisture detection circuit detects when the block of superabsorbent polymer no longer contacts the one or more electronic components, and provides an alert indicating a lack of moisture. The alert can include a visual alert, an audio alert, and an electronic message. The dryness sensor could be used, for example, to monitor the moisture content of soil in a pot that has a house plant growing in the pot.

Figures 1, 2, 3:
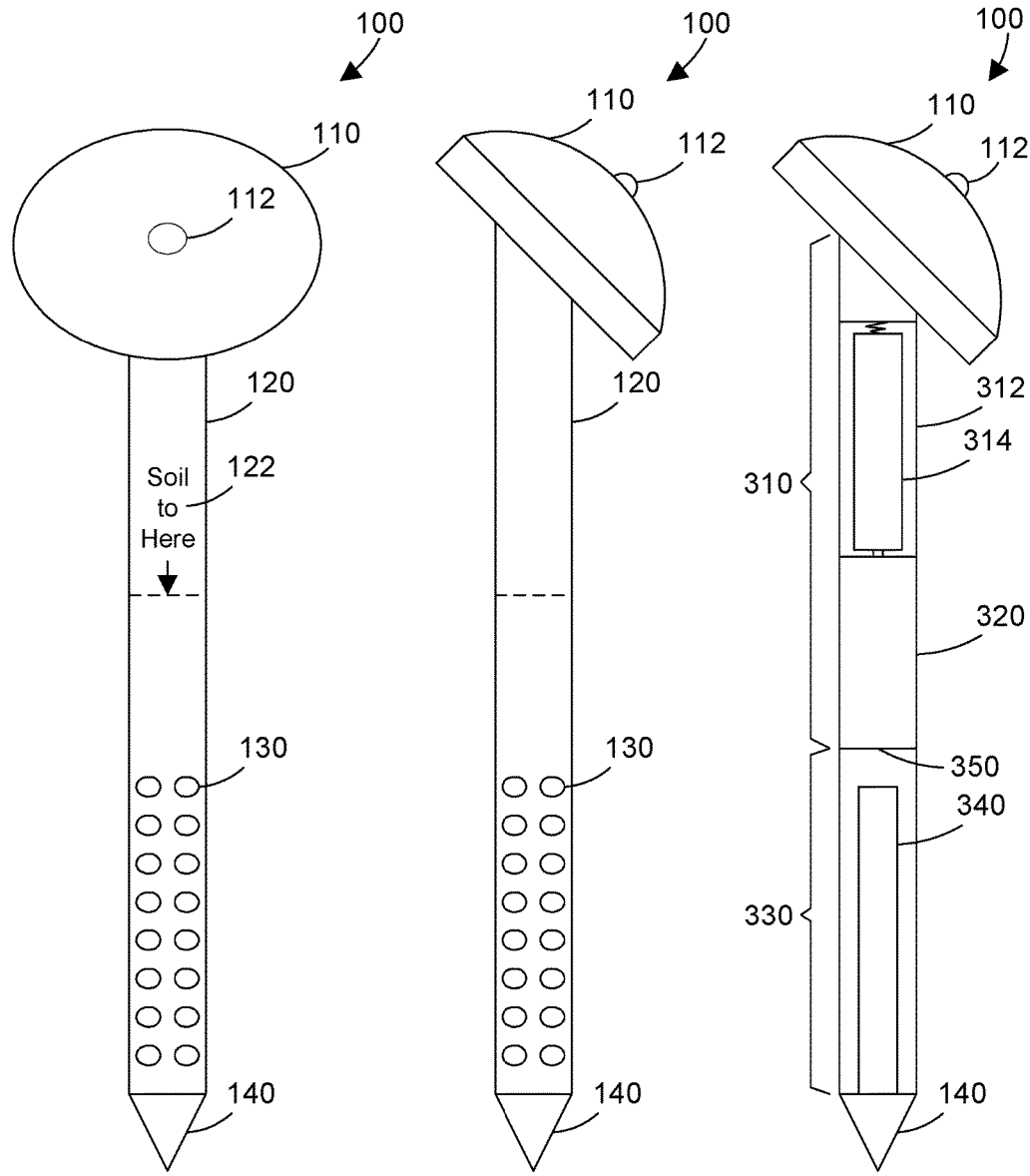
FIG. 1 is front view of a first implementation of a dryness sensor for sensing lack of moisture in soil near a plant.
FIG. 2 is a side view of the dryness sensor shown in FIG. 1.
FIG. 3 is a partial cross-sectional side view of the dryness sensor shown in FIG. 2.

One example configuration for a dryness sensor used to monitor soil moisture is shown in FIGS. 1-3. FIG. 1 is a front view of the dryness sensor 100 while FIG. 2 is a side view of the dryness sensor 100. Dryness sensor 100 includes a head portion 110 that can optionally include an electronic indicator 112, a shaft portion 120, and a tip portion 140. The head portion 110 preferably includes one or more solar cells that charge one or more batteries in the dryness sensor 100 from ambient light. The indicator 112 can be a visual indicator or an audio indicator that can provide an indication when the dryness sensor detects a lack of moisture. For example, indicator 112 could be a light-emitting diode (LED) that flashes when the dryness sensor detects a lack of moisture.

The shaft portion 120 preferably includes one or more openings that allow liquid to pass into the interior of the shaft portion 120. The shaft portion 120 may include text or other symbols to indicate the correct depth for installing the dryness sensor 100. For the specific example shown in FIG. 1, the dryness sensor 100 includes the text "Soil to Here" 122 with an arrow that points to a line that indicates the correct depth in the soil for the dryness sensor 100. For the specific example in FIGS. 1 and 2, shaft portion 120 includes multiple holes 130 that allow liquid to pass through the exterior of the shaft portion 120 into the interior of the shaft portion 120, and more particularly, into a moisture detection chamber as discussed further below. Shaft portion 130 could optionally include a screen mesh (not shown in FIGS. 1 and 2) on the interior of the shaft portion 120 and overlying the holes 130 so particles of soil and other impurities cannot pass into the interior of the shaft portion 120. The tip portion 140 preferably includes a point that allows the dryness sensor 100 to be easily pushed into soil.

FIG. 3 shows a partial cross-sectional view of the dryness sensor 100 shown in FIG. 2 to illustrate some possible features within the dryness sensor 100. The dryness sensor 100 preferably includes a moisture detection chamber 330 in a lower portion and an upper region 310 that includes a housing 320 for electronics and a battery holder 312 that holds one or more batteries, such as battery 314 shown in FIG. 3. Battery 314 is most preferably a rechargeable battery so the battery 314 may be recharged by one or more solar cells on the head portion 110.

The electronics within housing 320 preferably include one or more electronic components at an interface 350 region of the moisture detection chamber 330. Examples of suitable electronic components are shown in FIGS. 4, 5, 7 and 8, which are discussed in detail below. The moisture detection chamber 330 preferably includes absorbable material 340 that increases in size as it absorbs liquid and decreases in size as it loses liquid. The walls of moisture detection chamber 330 preferably constrain the absorbable material 340 such that the absorbable material 340 cannot exceed the size of the moisture detection chamber 330. The most preferred absorbable material 340 is known as superabsorbent polymer (SAP), which is well-known in the field of disposable diapers and children's toys. Disposable diapers typically include granules of SAP that allow the diaper to soak up large amounts of liquid relative to their mass. Some children's toys known as expandable water toys are made of SAP. These toys are typically a block of SAP shaped to resemble an animal, such as a fish, a whale, a dinosaur, etc. When the toy is placed in water, it absorbs the water and grows to a size much larger than its original size due to the absorption of water. As the toy loses water by drying out, it shrinks to a smaller size due to the loss of water. When completely dried out, the toy typically returns to its original size.

SAP has not been used in the art of moisture sensors. Most moisture sensors include sophisticated electronics that measure moisture to a precision that is not needed for the simple application of determining when the soil near a plant is dry and needs water. Whether the moisture in the soil is 62% or 55% is unimportant in most applications. What is needed most is not really a moisture sensor, but a "dryness sensor" of sorts that can provide an indication of when the soil needs water. As long as the moisture is above some threshold, the soil does not need water. But once the water level drops to be below some threshold, the soil needs water. This is an ideal application for house plants. A person can place a dryness sensor as disclosed herein in the soil of a house plant, and not worry about watering the plant until the dryness sensor indicates a lack of moisture in the soil. One suitable SAP could be, for example, SAP cubes from M2 Polymer Technologies, Inc. in West Dundee, Ill.

The absorbable material 340 shown in FIG. 3 is preferably a cylindrical block of SAP. The precise geometric configuration and dimensions may vary within the scope of the disclosure and claims herein. A block of SAP as used herein may include any suitable geometric configuration and dimensions, including the use of multiple blocks of SAP. For example, instead of using a single elongated cylindrical block of SAP, multiple shorter cylindrical blocks of SAP could be stacked. Regardless of the specific geometric configuration and dimensions of the absorbable material 340, when the absorbable material 340 absorbs a first threshold of liquid, it expands to contact one or more electronic components at the interface 350. When the absorbable material 340 loses liquid, its size decreases until the absorbable material 340 no longer contacts the one or more electronic components at the interface 350. For the application of a dryness sensor for soil as shown in FIGS. 1-3, water in the soil passes through the one or more holes 130, which are openings between an external portion of the dryness sensor 100 and the moisture detection chamber 330 so the water that contacts the external portion of the dryness sensor can pass into the moisture detection chamber 330 to contact the absorbable material 340. The absorbable material 340 increases in size as it absorbs the water, eventually pressing against one or more electronic components at the interface 350 of the moisture detection chamber. Moisture detection circuitry is preferably located within housing 320 and is connected to the one or more electronic components at the interface 350 such that when the absorbable material contacts the one or more electronic components at the interface 350, the moisture detection circuitry is in a first state that indicates presence of moisture. As the absorbable material 340 loses moisture over a period of days or weeks, the absorbable material decreases in size until it no longer contacts the one or more electronic components at the interface 350. The moisture detection circuitry detects when the absorbable material no longer contacts the one or more electronic components at the interface 350, and in response, is in a second state that indicates a lack of moisture.

While SAP is disclosed as the preferred material for the absorbable material, other materials could be used within the scope of the disclosure and claims herein. For example, a tight-celled sponge could be used. A block of sodium polyacrylate could be used. A block of tightly-packed cotton could be used. Any suitable material that increases in size as it absorbs liquid and decreases in size as the amount of absorbed liquid is reduced is within the scope of the disclosure and claims herein.

Figure 4:
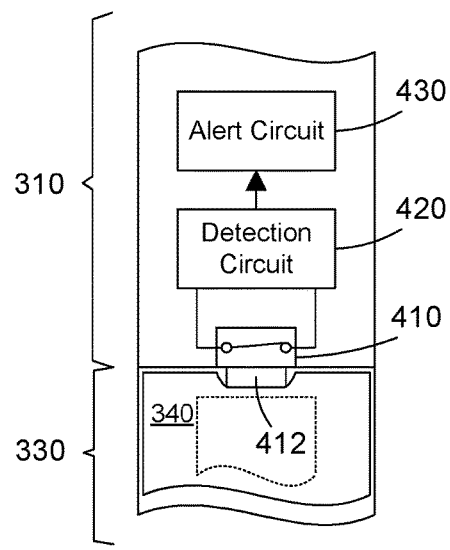
FIG. 4 is an enlarged side cross-sectional view of a portion of the dryness sensor shown in FIGS. 1-3 showing a normally-open momentary push-button switch as a first implementation for sensing moisture that is pressed as a result of the absorbable material swelling with moisture.
Figure 5:
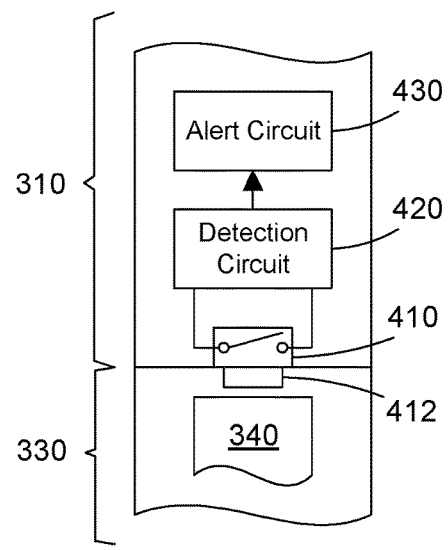
FIG. 5 shows the dryness sensor in FIG. 4 after the absorbable material has shrunk by the loss of moisture to no longer press the momentary push-button switch.

A first specific implementation for the dryness sensor 100 in FIGS. 1-3 is shown in FIGS. 4 and 5. Referring to FIG. 4, this example shows the electronic component at the interface 350 is a momentary single-pole single-throw pushbutton switch 410 that includes a pushbutton 412 that, when pressed, closes the switch 410 as shown in FIG. 4. When the pushbutton 412 is not pressed, as shown in FIG. 5, the switch 410 is open as shown in FIG. 5. FIG. 4 shows part of the absorbable material 340 in a state after it has absorbed liquid, thereby expanding and pressing the pushbutton 412. Note the dotted line in FIG. 4 indicates the size of the absorbable material before it absorbs liquid. As the liquid in the absorbable material 340 is reduced, it reduces in size as shown at 340 in FIG. 5. As can be seen in FIG. 5, the reduced size of absorbable material 340 in FIG. 5 makes the absorbable material not push the momentary push-button any longer, which causes the switch 410 to open. The detection circuit 420 detects when the switch 410 is open, and changes to a second state that indicates a lack of moisture.

In the specific implementation in FIGS. 4 and 5 that uses a momentary pushbutton switch, the pushbutton switch preferably includes mechanical hysteresis such that once the pressure on the pushbutton decreases to a certain level, the switch will switch from its closed state in FIG. 4 to its open state in FIG. 5. The built-in mechanical hysteresis in the switch will assure the switch does not chatter or alternate between open and closed states at the point when the switch changes state. The mechanical hysteresis thus causes the switch to change state when the pressure on the switch decreases to some threshold value, but once the switch changes state, more pressure is required to change the state of the switch again. Note the force required to actuate the pushbutton can vary according to the specific design of the dryness sensor.

Figure 6:
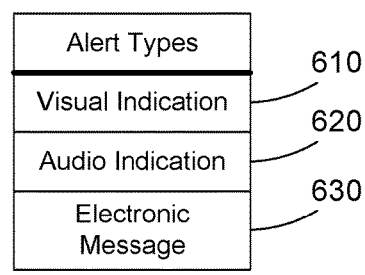
FIG. 6 is a table showing three examples of suitable alert types.

Switch 410 is one suitable example of an electronic component at the interface 350 of the dryness sensor chamber 330 shown in FIG. 3. Switch 410 is preferably coupled to the detection circuit 420, which is coupled to an alert circuit 430. When the absorbable material 340 presses the pushbutton 412 as shown in FIG. 4, the detection circuit 420 is in a first state that indicates presence of moisture above a first threshold value, in which state the detection circuit 420 does not signal to the alert circuit 430 that an alert should be provided. When the absorbable material 340 decreases in size to the point it no longer presses the pushbutton 412, as shown in FIG. 5, the detection circuit 420 is in a second state that indicates a lack of moisture, i.e., moisture below a second threshold value, in which state the detection circuit 420 signals to the alert circuit 430 that an alert should be provided. Three different alert types are shown in FIG. 6, and include a visual indication 610, an audio indication 620, and an electronic message 630. Visual indication 610 can be any suitable visual indication, including without limitation an illuminated red light, a blinking green LED, etc. The audio indication 620 can be any suitable audio indication, including without limitations an electric beep such as from a piezoelectric beeper, a constant tone, a periodic chirp, etc. The electronic message 630 can be any suitable message to any external device. For example, electronic message 630 could include without limitation a text message, an e-mail, or any other suitable electronic message. The electronic message 630 is preferably sent on a wireless interface to a device external to the dryness sensor. For example, the electronic message 630 could be sent via a Wi-Fi interface to an external electronic device. In the alternative, the electronic message could be sent via a Bluetooth interface to an external electronic device. In the most preferred implementation, the electronic message 630 is sent to a software app running on a user's mobile phone, which provides a notification that moisture is needed in response to the received electronic message.

Detection circuit 420 in FIGS. 4 and 5 can include any circuitry capable of detecting the difference between an open and a closed switch. For example, detection circuit 420 could be a digital circuit that has an open-drain output pulled high by a pull-up resistor, with the closing of switch 410 pulling the open-drain output low, and the opening of the switch 410 causing the open-drain output to be pulled high by the pull-up resistor. Detection circuit 420 could be a suitable analog circuit that distinguishes between a closed switch and an open switch. For example, the switch closing could cause a resistor to be connected in parallel with another resister, thereby reducing the resistance, which causes some effect in the detection circuit, such as changing voltage across the resistor, changing frequency of an oscillator that includes the resistor, etc. The switch closing could also switch one or more electronic components in an operational amplifier circuit such that the output of the operational amplifier is low when the switch is closed and is high when the switch is open, or vice versa. In another implementation, the detection circuit could be digital or analog circuitry within a microcontroller. One skilled in the art will recognize there are numerous different detection circuits that could detect between an open switch and a closed switch, and could thus be used as detection circuit 420 in FIGS. 4 and 5. The disclosure and claims herein extend to any suitable type of detection circuit that can detect a difference between a closed switch and an open switch, including both detection circuits that are currently known as well as those developed in the future.

Figure 7:
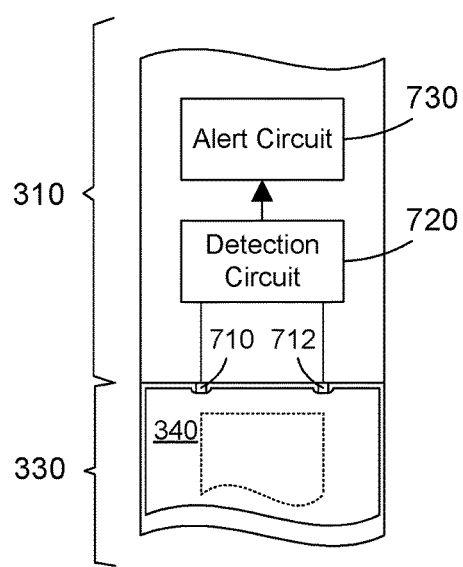
FIG. 7 is an enlarged side cross-sectional view of a portion of the dryness sensor shown in FIGS. 1-3 showing two electronic contacts as a second implementation for sensing moisture as a result of the absorbable material swelling with moisture.
Figure 8:
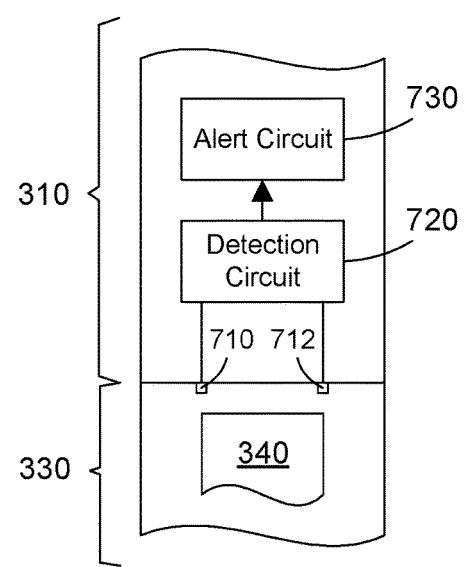
FIG. 8 shows the dryness sensor in FIG. 7 after the absorbable material has shrunk by the loss of moisture to no longer contact the electronic contacts.

A second implementation for the dryness sensor 100 in FIGS. 1-3 is shown FIGS. 7 and 8. Detection circuit 720 is connected to two electrical contacts 710 and 712. The electrical contacts 710 and 712 in FIGS. 7 and 8 and the momentary pushbutton switch 410 in FIGS. 4 and 5 are examples of electronic components at the interface of the moisture detection chamber that are coupled to a detection circuit. When the absorbable material 340 absorbs liquid, it increases in size, as shown in FIG. 7 as 340 increasing from the original size shown in the dotted line to the size shown in FIG. 7. Note the increase in size of the absorbable material 340 means the absorbable material touches both electrical contacts 710 and 712, as shown in FIG. 7. Most liquids have some electrical conductance that allows detecting a difference between when the absorbable material does not touch the electrical contacts 710 and 712, as shown in FIG. 8, and when the absorbable material touches the electrical contacts 710 and 712, as shown in FIG. 7. Distilled water has a very high electrical resistance, but normal tap water includes minerals and sometimes impurities that reduce the electrical resistance of the water. In addition, particles in soil can dissolve in the water, reducing the electrical resistance of the water. The detection circuit 720 detects a reduced resistance between electrical contacts 710 and 712 when the absorbable material 340 touches both electrical contacts 710 and 712, which corresponds to a first state that indicates moisture above a first threshold value. As the absorbable material 340 loses moisture, its size reduces until it no longer contacts either of the electrical contacts 710 and 712, which increases the resistance between the electrical contacts 710 and 712, causing the detection circuit 720 to be in a second state that indicates a lack of moisture. When the detection circuit 720 is in the first state when the absorbable material contacts both electrical contacts 710 and 712 illustrated in FIG. 7, which indicates adequate moisture, the detection circuit 720 does not signal the alert circuit 730 to create an alert. When the detection circuit 720 is in the second state when the absorbable material does not contact both electrical contacts 710 and 712 illustrated in FIG. 8, which indicates a lack of moisture, the detection circuit 720 signals the alert circuit 730 to create an alert.

Detection circuit 720 could be any circuit, digital or analog, that is capable of detecting the difference between a first state when the absorbable material 340 contacts both electrical contacts 710 and 712 as shown in FIG. 7, and a second state when the absorbable material 340 does not contact both electrical contacts 710 and 712. Detection circuit 720 could detect any suitable change between the two electrical contacts 710 and 712, including resistance, and/or capacitance and/or inductance. For example, an operational amplifier circuit could include a resistor that comprises the resistance between electrical contacts 710 and 712, where a reduced electrical resistance between the electrical contacts 710 and 712 caused by the absorbable material 340 contacting both electrical contacts 710 and 712 causes the output of the operational amplifier to be in a first state, while an increased electrical resistance between the electrical contacts 710 and 712 caused by the absorbable material 340 not contacting both electrical contacts 710 and 712 causes the output of the operational amplifier to be in a second state. One skilled in the art will recognize there are many different types of detection circuits that could detect the difference in electrical properties between electrical contacts 710 and 712, all of which are within the scope of the disclosure and claims herein.

The detection circuit 720 could include built-in electronic hysteresis so an alert is only sent to the alert circuit 730 after some period of time after the detection circuit 720 detects a stable signal on the electrical contacts 710 and 712. As the absorbable material loses moisture, it size is reduced. But there may be a time when the absorbable material is only lightly touching the electrical contacts 710 and 712, which may cause the detection circuit to detect a change to the second state, then a change back to the first state, then a change to the second state, and so on. The detection circuit 720 preferably includes hysteresis that prevents changing from the first state to the second state until a sufficient time passes without the detection circuit 720 detecting a change back to the first state. This can be accomplished in any suitable way. For example, a processor in detection circuit 720 could set a timer each time the detection circuit detects a change at the electrical contacts 710 and 712. When the detection circuit detects a change back to the original state before the timer expires, the detection circuit does not change to the second state. When the detection circuit detects that no changes back to the original state have occurred when the timer expires, the detection circuit 720 changes to the second state. The hysteresis in the detection circuit 720 prevents the detection circuit from changing state back and forth at the transition point when the absorbable material ceases to contact both electronical contacts 710 and 712. This assures the detection circuit actually changes from the first state indicating moisture to the second state indicating a lack of moisture only after some time has elapsed without detecting a change back at the electrical contacts 710 and 712.

Figure 9:
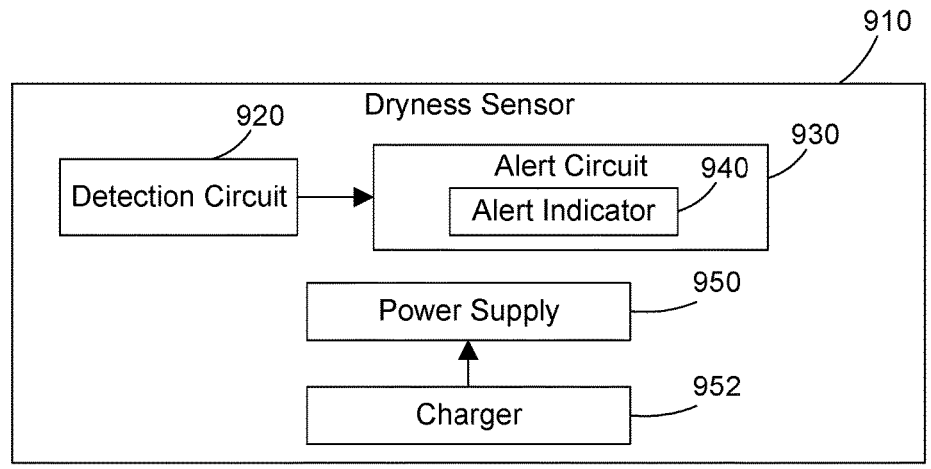
FIG. 9 is block diagram of a first suitable implementation for the dryness sensor.

FIG. 9 is a block diagram of a first exemplary implementation of the dryness sensor disclosed herein, shown as dryness sensor 910. Dryness sensor 910 could represent the internal functional blocks within the dryness sensor 100 shown in FIGS. 1-3. The dryness sensor 910 includes a moisture detection circuit 920 connected to an alert circuit 930 that includes an alert indicator 940. A power supply 950 provides power to the detection circuit 920, the alert circuit 930 and the alert indicator 940. A charger 952 can be optionally included to charge the power supply 950. In a preferred implementation, power supply 950 comprises one or more rechargeable direct current (DC) batteries, such as one or more AAA or AA batteries known in the art. The charger 952 can include any suitable charger, and preferably includes one or more solar cells on the head portion of the dryness sensor that allows charging the rechargeable battery or batteries from ambient light. As described above with reference to FIG. 6, the alert indicator can be a visual indicator, an audio indicator, or an electronic message sent to an external electronic device, such as a mobile phone. In one very simple implementation of dryness sensor 910, the detection circuit provides a digital signal in a first state when the electronics at the interface indicate a closed circuit, such as in FIGS. 4 and 7, and provides a digital signal in a second state when the electronics at the interface indicate an open circuit, such as in FIGS. 5 and 8. When the digital signal output from the detection circuit 920 is in the first state, the alert circuit 930 does not activate the alert indicator 940. When the digital signal output from the detection circuit 920 is in the second state, the alert circuit 930 activates the alert indicator 940 to indicate a lack of moisture. Of course, more sophisticated electronics could be included in the detection circuit and/or the alert circuit, such as state machines or other electronics within the scope of the disclosure and claims herein.

Figure 10:
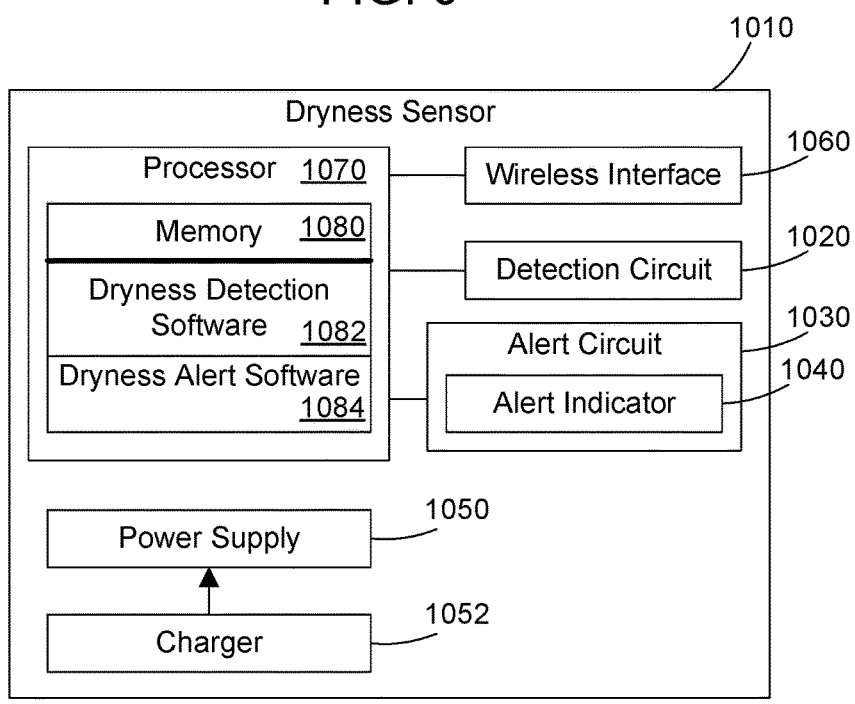
FIG. 10 is a block diagram of a second suitable implementation for the dryness sensor.

FIG. 10 is a block diagram of a second exemplary implementation of the dryness sensor disclosed herein, shown as dryness sensor 1010. Dryness sensor 1010 could represent the internal functional blocks within the dryness sensor 100 shown in FIGS. 1-3. The dryness sensor 1010 includes a detection circuit 1020, an alert circuit 1030 with a corresponding alert indicator 1040, a power supply 1050, an optional charger 1052, a wireless interface 1060, a processor 1070, and a memory 1080. The detection circuit 1020 includes connections to one or more electronic components at the interface of the moisture detection chamber, such as the pushbutton switch shown in FIGS. 4 and 5 and the electrical contacts 710 and 712 shown in FIGS. 7 and 8. Of course, other electronic components could be used at the interface of the moisture detection circuit, which are within the scope of the disclosure and claims herein. For example, a pressure transducer or strain gauge transducer could be used. The alert circuit 1030 and alert indicator 1040 can function similarly to the alert circuit 930 and alert indicator 940 discussed above, or could have different functions. The power supply 1050 and charger 1052 are similar to the power supply 950 and charger 952 in FIG. 9 described above, and most preferably include one or more rechargeable batteries for the power supply 1050 and optionally include one or more solar cells for the charger 1052.

The processor 1070 is most preferably a microcontroller as is known in the art. Microcontrollers often include on-board memory, so memory 1080 is shown as part of processor 1070. Note, however, that memory 1080 could also be separate from the processor 1070. The memory 1080 preferably includes dryness detection software 1082 and dryness alert software 1084. The dryness detection software 1082 receives input from the detection circuit 1020, or directly from the electronic components at the interface of the moisture detection chamber, and is in a first state indicating moisture, and changes to a second state indicating a lack of moisture when indicated by the detection circuit 1020 or the electronic components at the interface of the moisture detection chamber. When the dryness detection software 1082 changes to the second state to indicate a lack of moisture, it provides notification to the dryness alert software 1084, which then signals the alert circuit 1030 to activate the alert indicator 1040. Note the dryness detection software 1082 and dryness alert software 1084 are shown separate in FIG. 10, but could be combined so a single software program performs both functions. In addition, the detection circuit 1020 and alert circuit 1030 may not be needed depending on the microcontroller used as the processor 1070. Some microcontrollers include one or more inputs that could function as the detection circuit 1020, and also include one or more outputs that could function as the alert circuit 1030. In this configuration, the electronic components at the interface of the moisture detection chamber could be input directly to the processor 1070, and the processor 1070 could directly drive an alert indicator 1040. The wireless interface 1060 is used when the alert indicator 1040 sends an electronic message indicating a lack of moisture to an electronic device external to the dryness sensor, such as a mobile phone. The wireless interface 1060 could be a Wi-Fi interface that allows sending an e-mail message. The wireless interface 1060 could be a Bluetooth interface that allows sending a message to an electronic device in close proximity to the dryness sensor. The wireless interface 1060 could be an interface to a mobile phone network that allows the dryness sensor to send a text message to a mobile phone. The wireless interface 1060 could be any suitable wireless interface for communicating with an external electronic device using any suitable communication method or protocol, whether currently known or developed in the future.

Figure 11:
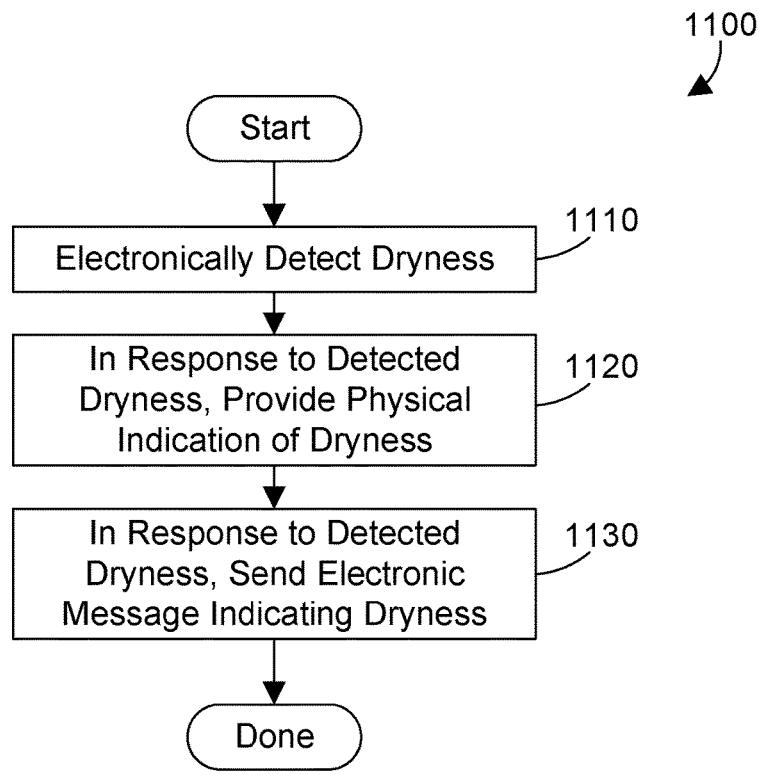
FIG. 11 is a flow diagram of a method for sensing dryness using the dryness sensor disclosed and claimed herein.

FIG. 11 shows a method 1100 for detecting a lack of moisture, or dryness, in accordance with the disclosure and claims herein. Method 1100 electronically detects dryness (step 1110). In response to the detected dryness, a physical indication of dryness is provided (step 1120). Physical indications of dryness could include one or more visual indications, and/or one or more audio indications. In response to the detected dryness, an electronic message may be sent indicating dryness (step 1130). The electronic message is preferably sent to a device external to the dryness sensor, such as a mobile phone. Note that step 1120 may not be performed when the dryness sensor does not include any visual indicators or audio indicators. Step 1130 may not be performed when the dryness sensor does not include a wireless interface that supports sending the electronic message. When the dryness sensor includes one or more visual indicators and/or audio indicators, and also includes a wireless interface, both of steps 1120 and 1130 could be performed.

Figure 12:
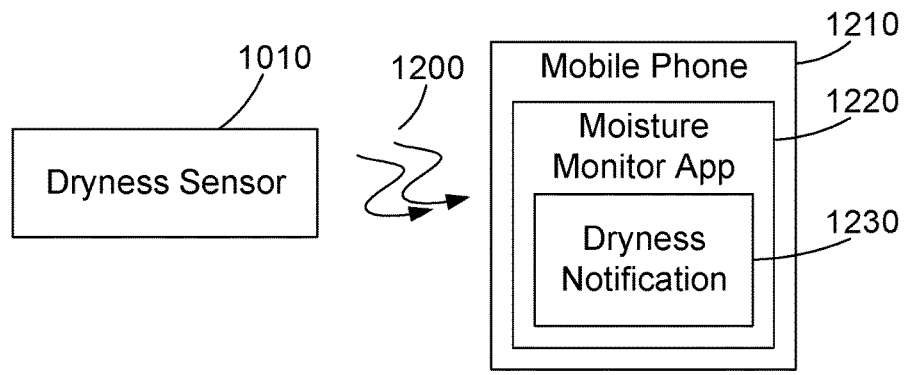
FIG. 12 is a block diagram showing a dryness sensor providing an electronic message indicating dryness to a moisture monitoring app on a mobile phone.

FIG. 12 shows the dryness sensor 1010 in FIG. 10 sending an electronic message via wireless communications 1200 to a mobile phone 1210. In one specific implementation, the mobile phone 1210 includes a moisture monitor app 1220 that can receive messages from multiple dryness sensors, and can provide a dryness notification 1230 to a user of the mobile phone 1210. A simple example will illustrate. Let's assume a person has six different house plants, and installs six different dryness sensors, one in the soil of each house plant. The user could configure the moisture monitor app 1220 to recognize each of the six dryness sensors. For example, the user could provide a name, plant type or location corresponding to each dryness sensor. When one of the dryness sensors sends a message indicating dryness as shown in FIG. 12, the moisture monitor app 1220 provides a dryness notification 1230 to the user of the mobile phone so the user will know that the plant corresponding to the moisture monitor that sent the message needs to be watered. The dryness notification 1230 can include a vibration, a ring tone, an audio sound, flashing lights, an e-mail or text message, or any other suitable notification to the user. One of the biggest problems with keeping houseplants healthy is people tend to over-water their houseplants. The dryness sensor herein solves this problem, allowing a user to water a plant, then wait until the user receives a notification that the plant needs to be watered again. The dryness sensor thus helps a user provide the optimal amount of water to the plants that will ensure the vigor and vitality of the plants.

The size and shape of the absorbable material could be adjusted to provide different thresholds for indicating dryness. A desert cactus plant needs only a fraction of the water needed by a lush, green plant that typically grows in a rain forest. The dryness sensor disclosed herein can be calibrated for the water needs of a particular plant by varying the size and/or shape of the absorbable material. For example, if the absorbable material has an initial size and shape that puts the top of the absorbable material very close to the electronic components at the interface of the moisture detection chamber, when the absorbable material expands, it will contact the electronic components very quickly and will continue to absorb moisture, which means the absorbable material will have to release water until it reaches nearly its original size before indicating dryness. Such a configuration would be suitable, for example, for a desert plant such as an Aloe Vera plant or a cactus, because once the absorbable material absorbs water, it will take a long time for the absorbable material to shrink down to the point where the dryness sensor will signal dryness. On the other end of the spectrum, with lush leafy plants that require a lot of water, the absorbable material may have an initial size and shape that puts the top of the absorbable material far away from the electronic components at the interface of the moisture detection chamber, such that the absorbable material does not reach the electronic components until it is nearly saturated. In this configuration, the absorbable material will lose contact with the electronic component(s) after losing a relatively small amount of moisture, which will cause the dryness sensor to signal dryness much sooner. Many different configurations of absorbable material between these two extremes can be made to accommodate plants that have differing water requirements.

Figure 13:
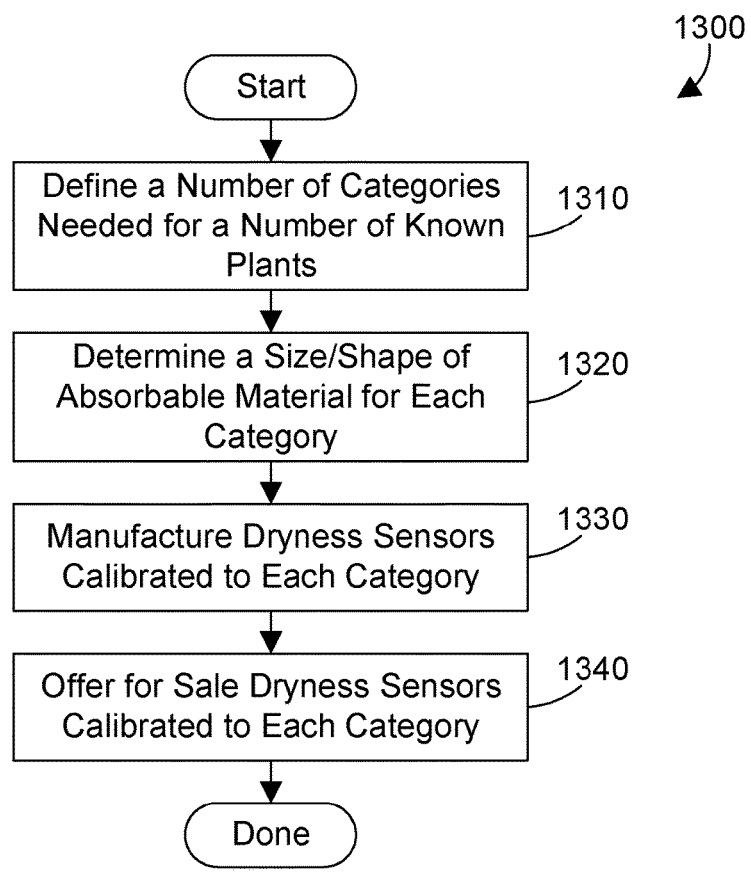
FIG. 13 is a flow diagram of a method for creating dryness sensors calibrated to different categories, and offering those dryness sensors for sale.

Referring to FIG. 13, method 1300 is a way to provide different dryness sensors to correspond to plants with different water needs. First, define a number of categories needed for a number of known plants (step 1310). These categories can be defined based on any suitable criteria, but are most preferably defined based on the water needs of each plant. For example, the categories can be defined based on water needs in terms of inches of water per week. Let's assume we define four categories, a first for plants that need less than 0.5 inch of water per week, a second for plants that need 0.5 to 1.0 inches of water per week, a third for plants that need 1.0 to 2.0 inches of water per week, and a fourth for plants that need more than 2.0 inches of water per week.

Once the categories are defined in step 1310, determine a size and shape of absorbable material for each category (step 1320). This will depend on the specific absorbable material used. For example, dimensions for a cotton cylinder will be much different than dimensions for a cylinder made of SAP. However, one skilled in the art will recognize that different dimensions for the absorbable material will result in the dryness sensor indicating dryness at different points of moisture in the soil. Once the suitable sizes and shapes of absorbable material are determined in step 1320, these different sizes and shapes of absorbable material can be manufactured and assembled into dryness sensors that are calibrated to signal dryness at different moisture levels (step 1330). These dryness sensors calibrated for each category may then be offered for sale (step 1340). Method 1300 is then done.

The preferred implementations for the dryness sensor shown in the figures and discussed above is for a dryness sensor that detects water in soil. However, other embodiments or implementations are equally within the scope of the disclosure and claims herein. The term "moisture" as used herein refers to any liquid that can be absorbed by any suitable absorbable material. For example, the dryness sensor disclosed herein could be used as part of a plug-in air freshener, where the scented liquid that provides the scent of the air freshener is absorbed by the absorbable material, and when the level of scented liquid is reduced by use to a level where the scented liquid is nearly gone, the dryness sensor could provide an indication that the scented liquid is nearly gone, such as a blinking LED, an audio tone or chirp, or an electronic message to a user's mobile phone. The disclosure and claims herein expressly extend to detecting a lack of any suitable liquid using any suitable absorbable material, whether currently known or developed in the future.

Figure 14:
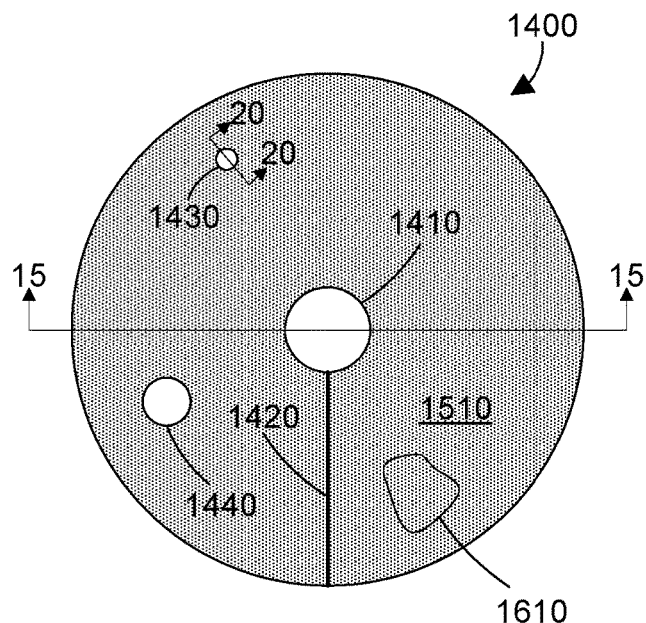
FIG. 14 is a top view of one suitable sample implementation for an irrigation mat.
Figure 15:
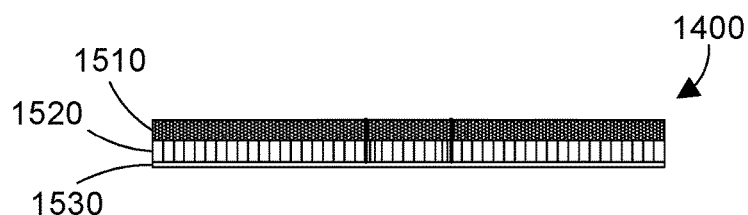
FIG. 15 is a side cross-sectional view of the irrigation mat in FIG. 14 taken along the line 15-15.
Figure 16:
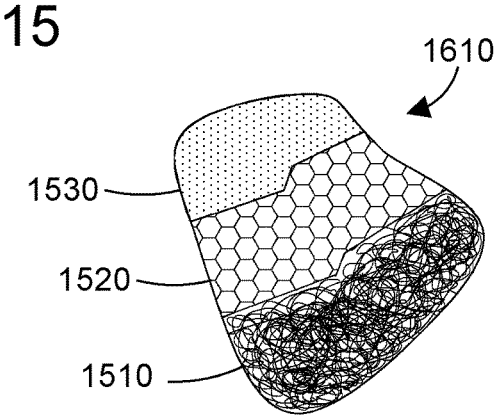
FIG. 16 is an enlarged portion of the irrigation mat in FIG. 14 showing a sample configuration for each of the three layers shown in FIG. 15.

Referring to FIGS. 14-16, one sample configuration for an irrigation mat 1400 is shown. The irrigation mat 1400 is circular, with a circular open middle 1410 and a slit 1420 that allows the irrigation mat 1400 to be placed around a plant in the same manner that known tree rings are placed around trees. The irrigation mat 1400 may optionally include a fertilizer port 1430 and may also optionally include an open port 1440 through which a dryness sensor may be placed into the soil below to detect the moisture level in the soil underlying the irrigation mat 1400. The irrigation mat preferably includes three layers, shown in the cross-sectional view in FIG. 15, which is a cross-section of the irrigation mat 1400 in FIG. 14 taken along the line 15-15. The top layer 1510 is any suitable material that is substantially permeable to water so the water, when poured on the top layer 1510, will flow without substantial obstruction to the water cells 1520 below. The water cells 1520 each have a substantially open top to receive water poured through the top layer 1510, and a substantially open bottom so the water in each cell is in contact with the semi-permeable bottom layer 1530. The water cells 1520 collectively form a water reservoir. The semi-permeable bottom layer 1530 is semi-permeable to water such that water passes from the water cells 1520 through the bottom layer 1530 at a controlled rate. In the most preferable implementation, the bottom layer 1530 allows water to pass through at a relatively slow rate, such that it takes a substantial period of time for the water in the water cells to pass through the bottom layer 1530 into the soil below. In one suitable example, it takes many hours for the water in the water cells to pass through the bottom layer 1530 into the soil below. In the most preferred example, it takes many days for the water in the water cells to pass through the bottom layer 1530 into the soil below. Examples of the three layers in FIG. 15 are shown in FIG. 16, which is an enlarged section 1610 of the irrigation mat 1400 shown in FIG. 14, with layers cut away to illustrate the configuration of each layer. The top layer 1510 is shown as a layer of fiber. One suitable fiber that could be used is coconut coir fiber available from Xiamen Green Field Co., Ltd. in Xiamen, China. Of course, a variety of other materials could be used, both natural and synthetic. Water cells 1520 are shown as a honeycomb-like structure that is open top and bottom, and includes individual hexagonal water cells that share side walls with each of its neighbors. Of course, the water cells could be in any suitable cross-sectional geometrical configuration, including square, rectangle, triangle, or any suitable polygon, or could even be a collection of random shapes. For example, if some of the water cells had a circular cross-section, the spaces between the circles would be non-circular in shape. This example shows the water cells can also have multiple different cross-sectional shapes. In addition, the size and number of water cells could vary greatly within the scope of the disclosure and claims herein. For example, with a relatively small size honeycomb configuration as shown in FIG. 16, there could be hundreds or thousands of water cells in an irrigation mat. On the other end of the spectrum, there could be very few water cells. For example, in the configuration shown in FIG. 14, four water cells could each cover a ninety degree quadrant of the circular mat. The disclosure and claims herein extent to any suitable number for the plurality of water cells. In the most preferred implementation, there are many water cells so the water in each cell is released to the soil below at a controlled rate through the semi-permeable membrane. One suitable implementation of the water cells is Ortho-Gel available from EdiZONE LLC in Alpine, Utah. Any suitable material that has multiple cells could be used as a water reservoir in the irrigation mat. In the most preferred implementation, the material that has multiple cells is a flexible material. However, it is equally within the scope of the disclosure and claims herein to provide a more rigid material, such as polypropylene.

The semi-permeable bottom layer 1530 could be any suitable material that allows water in the water cells to flow by the force of gravity through the bottom layer 1530 at a slow rate, such as hours or days. One specific semi-permeable bottom layer 1530 is needle punched weed barrier available from AGU in Shandong Sheng, China. In the most preferred implementation, the bottom layer 1530 is attached to the bottoms of the water cells using a suitable adhesive. Of course, any suitable attachment could be used. For example, the bottom layer 1530 could be thermally or chemically fused to the bottom of the water cells. In the most preferred implementation, the bottom layer 1530 substantially seals the bottom of each water cell.

Figure 17:
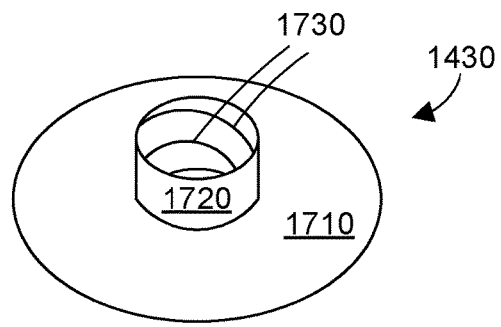
FIG. 17 is a perspective view of a fertilizer port in the irrigation mat shown in FIG. 14.
Figure 18:
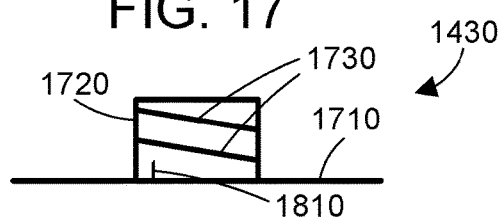
FIG. 18 is a side cross-sectional view of the fertilizer port.
Figure 19:
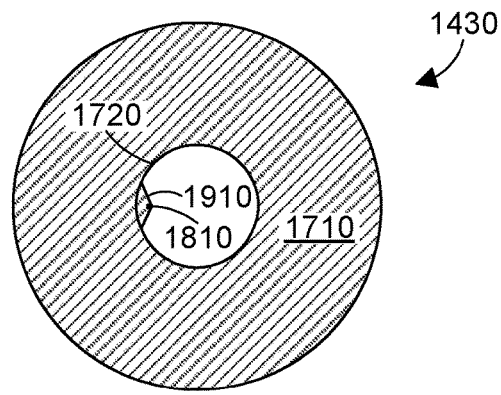
FIG. 19 is a top view of the fertilizer port.
Figure 20:
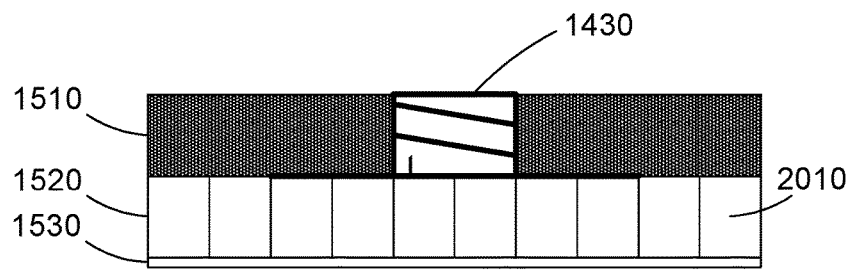
FIG. 20 is a side cross-sectional view of the fertilizer port shown in FIG. 14 taken along the line 20-20.

The irrigation mat 1400 shown in FIG. 14 includes an optional fertilizer port 1430. The fertilizer port 1430 allows a bottle of liquid fertilizer to be screwed onto threads on the fertilizer ports 1430 so the liquid fertilizer can flow by the force of gravity into the water cells, thereby allowing a combination of water and fertilizer to be released by the irrigation mat into the soil below. One suitable configuration for the fertilizer port 1430 is shown in FIG. 17. The fertilizer port 1430 preferably includes a flanged portion 1710 with a raised center portion 1720 that includes internal threads 1730 onto which a threaded bottle of liquid fertilizer may be screwed. As shown in FIG. 18, the fertilizer portion 1430 preferably includes a pointed barb 1810 that serves the function of piercing a foil top on a liquid fertilizer container as the liquid fertilizer container is screwed into the threaded center portion 1720. This allows for a mess-free application of fertilizer, by taking a bottle of liquid fertilizer that is sealed with a foil seal and screwing the bottle into the threaded center portion 1720, which causes the barb 1810 to pierce the foil seal, thereby allowing the contents of the liquid fertilizer bottle to flow by force of gravity into the water cells below. The barb 1810 may be on a portion 1910 of the fertilizer port that extends into the threaded center portion 1720, as shown in FIG. 19. The fertilizer port 1430 is shown in FIG. 20 installed between the top layer 1510 and the water cells 1520. Liquid fertilizer that flows from a fertilizer bottle into the water cells 1520 is released through the water cells 1520 into the soil below by the liquid in the water cells 1520 passing through the semi-permeable bottom 1530 by force of gravity. The view in FIG. 20 is a cross-sectional view of the fertilizer port 1430 in FIG. 14 taken along the line 20-20.

Figure 21:
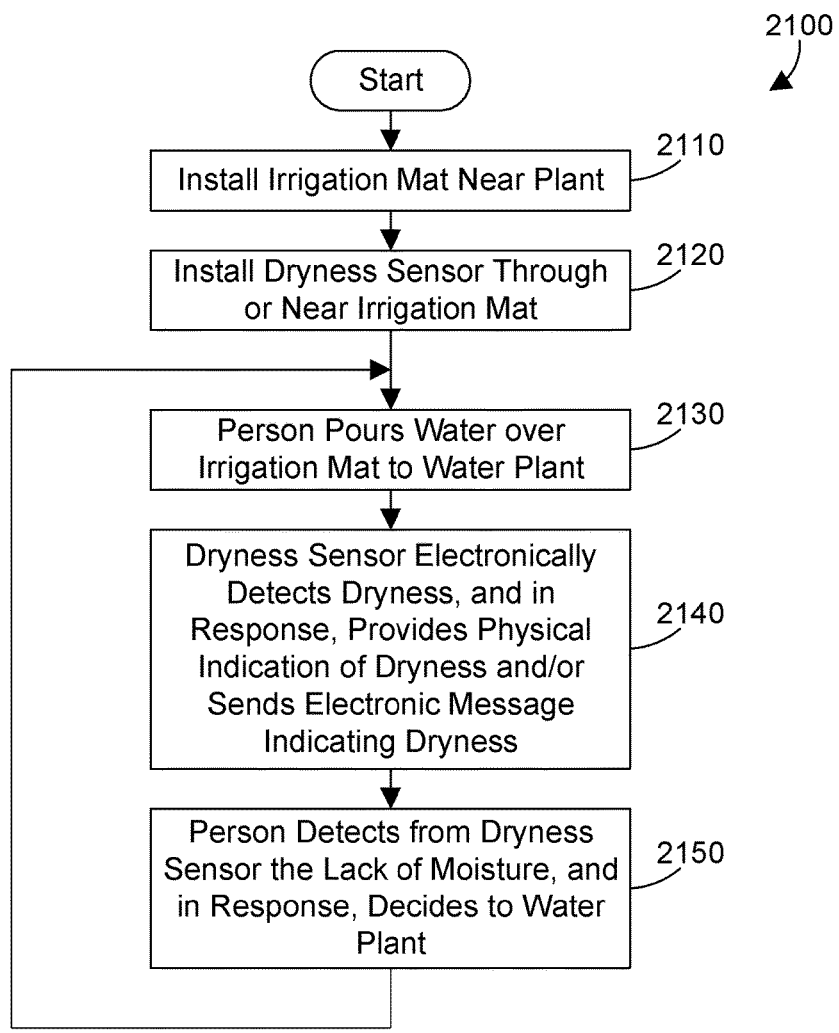
FIG. 21 is a flow diagram of one suitable method for installing and using a watering system.

A watering system in accordance with the disclosure and claims herein may include an irrigation mat, for example as shown in FIGS. 14-16, and a dryness sensor, for example as shown in FIGS. 1-10. Referring to FIG. 21, a method 2100 for using the watering system begins by installing the irrigation mat near a plant (step 2110). A dryness sensor is installed through or near the irrigation mat (step 2120). A person then pours water over the irrigation mat to water the plant (step 2130). By pouring the water over the irrigation mat, the water flows by force of gravity into the water cells, which then allows the water in the water cells to flow slowly through the semi-permeable membrane into the soil below. The dryness sensor electronically detects a lack of moisture, or dryness, in the soil, and in response, provides a physical indication of dryness and/or sends an electronic message indicating dryness (step 2140). The electronic message could be, for example, an alert sent to the user's mobile phone, as shown in FIG. 12. The person detects from the dryness sensor the lack of moisture, either from the physical indication or from the electronic message (or both), and in response decides to water the plant (step 2150). Method 2100 then loops back to step 2130, where the person pours water over the irrigation mat to water the plant (step 2130), and method 2100 then continues. Using the combination of the irrigation mat and dryness sensor as shown in FIG. 21, the water in the irrigation mat is slowly released into the soil below until the moistures sensor indicates lack of moisture in the soil near or beneath the irrigation mat. The watering system as disclosed herein thus minimizes overwatering and underwatering of plants.

Figure 22:
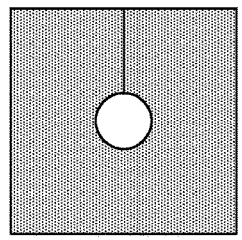
FIG. 22 is a top view of a square irrigation mat for use with one plant or one bunch of plants.
Figure 23:
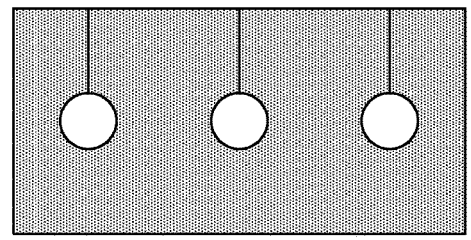
FIG. 23 is a top view of a rectangular irrigation mat for use with three plants or three bunches of plants.
Figure 24:
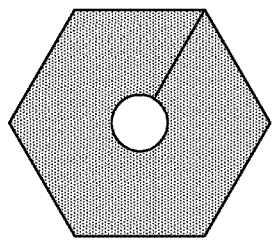
FIG. 24 is a top view of a hexagonal irrigation mat for use with one plant or one bunch of plants.
Figure 25:
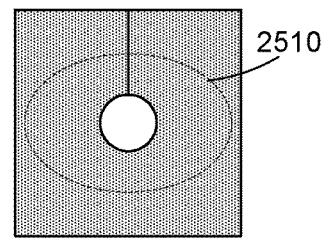
FIG. 25 is at top view of the square irrigation mat shown in FIG. 22 showing how the irrigation mat can be cut to a desired shape, such as an oval.

The irrigation mat may be manufactured in any suitable size, shape and configuration. Some suitable examples of different sizes and shapes are shown in FIGS. 14 and 22-25. The circular configuration in FIG. 14 is suitable, for example, for house plants in round pots. The square configuration in FIG. 22 is suitable, for example, for house plants in square pots. The rectangular configuration in FIG. 23 illustrates that a single irrigation mat can water multiple plants, as the irrigation mat 2300 includes openings for three different plants. The rectangular configuration in FIG. 23 could be used, for example, in a planter or pot that is rectangular in shape, or in a flowerbed that has three plants evenly spaced. The hexagonal configuration in FIG. 24 could be used, for example, in a pot that has a hexagon shape. Because the irrigation mat preferably includes an array of water cells, as shown in the honeycomb structure in FIG. 16, the irrigation mat may be cut to any desired shape. Thus, FIG. 25 illustrates the square irrigation mat in FIG. 22 could be cut to an oval shape 2510 to accommodate an oval pot. Cutting the irrigation mat to a desired size and shape is possible because of the array of water cells that make up the water reservoir in the irrigation mat. Cutting off some of the array of water cells leaves most of the remaining water cells substantially intact and able to perform their desired function. The disclosure and claims herein expressly extend to any suitable geometric size or shape for an irrigation mat, and to cutting an irrigation mat to any suitable size and shape.

Figure 26:
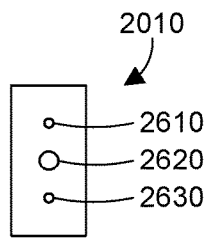
FIG. 26 is a view of a sidewall of one of the water cells in the irrigation mat showing one or more possible holes between adjacent water cells in one particular implementation.

The water cells in the irrigation mat may include holes between adjacent water cells. These holes can vary in size or location. For example, FIG. 26 shows the sidewall of one water cell shown in FIG. 20. The sidewall could include, for example, a hole 2610 near the top of the water cell. The hole 2610 will allow water to fill the water cell 2010 three fourths of the way before the water flows through the hole 2610 to the adjacent water cell. The sidewall could include, for example, a larger hole 2620 at the halfway point of the water cell. The hole 2620 will allow water to fill the water cell 2010 half way before the water flows through the hole 2620 to the adjacent water cell. The sidewall could include, for example, a hole 2630 near the bottom of the water cell. The hole 2630 allows water to fill the water cell 2010 one fourth of the way before the water flows through the hole 2630 into the adjacent water cell. Note the holes 2610 and 2630 in FIG. 26 are shown one size, while hole 2620 is shown a larger size. The disclosure and claims herein expressly extend to any suitable size or number of holes between sidewalls and any suitable location(s). Having holes between water cells allows the water to equalize between the water cells automatically, without the person watering the plant needing to make a conscious effort to fill all of the water cells. Of course, in some applications holes between water cells will not be desirable. For example, when the irrigation mat is used around a tree that has a mound of soil at the base of the tree, holes between water cells will allow the water to flow out of the higher water cells on top of the mound to the lower water cells at the bottom of the mound, resulting in the water spilling over the lower water cells. In this configuration, it would be desirable not to have holes between water cells in the irrigation mat.

The irrigation mat disclosed herein provides significant advantages when compared to not using any specific watering device or system. For example, in a potted plant, the irrigation mat can substantially cover the soil in the potted plant, which will prevent pets or small children from digging or playing in the dirt. By slowly releasing the water in the irrigation mat to the soil below at a controlled rate, significant contraction of the soil due to over-drying is avoided. In addition, the irrigation mat can be manufactured to contain any suitable quantity of water, depending on the plant being watered and the size of the irrigation mat. When more water is needed, the water cells can have a greater height. In the most preferred implementation, each irrigation mat has a specified capacity, and when the person waters the plant by pouring water onto the irrigation mat, the irrigation mat will maintain all of the specified capacity of water. The irrigation mat thus helps maintain a suitable level of moisture in the soil, thereby improving the health and vitality of the plant.

A plant watering system includes an irrigation mat that can be placed around a plant on top of the soil. The irrigation mat includes a water reservoir that holds water, and a slow-pass water permeable membrane that releases the water in the water reservoir in a slow manner so the soil around the plant is watered at a controlled rate. The irrigation mat may optionally include a threaded port where a container of liquid fertilizer can be placed so the liquid fertilizer is mixed with the water in the reservoir, allowing easily fertilizing the plant as it is watered. The plant watering system may also optionally include a dryness sensor that provides an alert indicating the water reservoir in the irrigation mat needs to be refilled.

The specific implementations for the irrigation mat shown in the figures include a center hole and a slit that allows the irrigation mat to be flexed and separated at the slit so the irrigation mat can be placed around an existing plant with the plant placed within the center hole. It is also within the scope of the disclosure and claims herein to provide an irrigation mat with a center hole without a slit, which could be placed, for example, before planting a plant. After placing the irrigation mat, a plant could then be planted in the soil within the center hole. In a different configuration, instead of the irrigation mat providing a circular center portion for receiving a plant, the irrigation mat could instead include an outer recess, such as a semicircle, that can be aligned with a semicircle on an adjacent irrigation mat. With this arrangement, the irrigation mats can be placed with minimal disruption of the plant. These and other variations are within the scope of the disclosure and claims herein.

A dryness sensor uses a block of superabsorbent polymer that absorbs liquid and increases in size as liquid is absorbed. When the block of superabsorbent polymer increases in size in the presence of liquid, the block of superabsorbent polymer contacts one or more electronic components coupled to a moisture detection circuit that provides an indication of moisture. When the block of superabsorbent polymer loses moisture, it decreases in size until the block of superabsorbent polymer no longer contacts the one or more electronic components. The moisture detection circuit detects when the block of superabsorbent polymer no longer contacts the one or more electronic components, and provides an alert indicating a lack of moisture. The alert can include a visual alert, an audio alert, and an electronic message. The dryness sensor could be used, for example, to monitor the moisture content of soil in a pot that has a house plant growing in the pot.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

The invention claimed is:

1. A dryness sensor comprising:
a moisture detection chamber comprising:
at least one opening between an external portion of the dryness sensor and the moisture detection chamber so liquid that contacts the external portion of the dryness sensor can pass into the moisture detection chamber;
at least one electronic component;
a block of superabsorbent polymer that increases in size when the block of superabsorbent polymer absorbs liquid and decreases in size as the block of superabsorbent polymer loses liquid, wherein the block of superabsorbent polymer has a first dimension that contacts the at least one electronic component when the block of superabsorbent polymer has a liquid content above a first threshold and has a second dimension that does not contact the at least one electronic component when the block of superabsorbent polymer has a liquid content less than a second threshold; and
a moisture detection circuit coupled to the at least one electronic component in the moisture detection chamber, the moisture detection circuit having a first state that indicates moisture when the block of superabsorbent polymer contacts the at least one electronic component and having a second state that indicates lack of moisture when the block of superabsorbent polymer does not contact the at least one electronic component.

2. The dryness sensor of claim 1 further comprising an alert circuit coupled to the moisture detection circuit that includes an alert indicator that provides an alert when the moisture detection circuit is in the second state.

3. The dryness sensor of claim 2 wherein the alert comprises a visual indication.

4. The dryness sensor of claim 2 wherein the alert comprises an audio indication.

5. The dryness sensor of claim 2 wherein the alert comprises an electronic message sent via a wireless interface to an electronic device.

6. The dryness sensor of claim 1 wherein electronic device comprises a mobile phone running a software app that receives the electronic message, and in response to the electronic message, provide a notification on the mobile phone.

7. The dryness sensor of claim 1 further comprising:
at least one rechargeable battery; and
at least one solar cell coupled to the at last one rechargeable battery so the solar cell charges the at least one rechargeable battery from ambient light.

8. The dryness sensor of claim 1 further comprising:
at least one processor;
a memory coupled to the at least one processor;
dryness detection software residing in the memory and executed by the at least one processor, the dryness detection software receiving an indication from the moisture detection circuit when the moisture detection circuit is in the second state that indicates a lack of moisture; and
dryness alert software residing in the memory and executed by the at least one processor, the dryness alert software receiving an indication from the dryness detection software when the moisture detection circuit is in the second state, and in response thereto, sending a signal to an alert circuit to activate an alert indicator.

9. A dryness sensor comprising:
a moisture detection chamber comprising:
at least one opening between an external portion of the dryness sensor and the moisture detection chamber so liquid that contacts the external portion of the dryness sensor can pass into the moisture detection chamber;
at least one electronic component;
a block of superabsorbent polymer that increases in size when the block of superabsorbent polymer absorbs liquid and decreases in size as the block of superabsorbent polymer loses liquid, wherein the block of superabsorbent polymer has a first dimension that contacts the at least one electronic component when the block of superabsorbent polymer has a liquid content above a first threshold and has a second dimension that does not contact the at least one electronic component when the block of superabsorbent polymer has a liquid content less than a second threshold;
a moisture detection circuit coupled to the at least one electronic component in the moisture detection chamber, the moisture detection circuit having a first state that indicates moisture when the block of superabsorbent polymer contacts the at least one electronic component and having a second state that indicates lack of moisture when the block of superabsorbent polymer does not contact the at least one electronic component;
an alert circuit coupled to the moisture detection circuit that includes an alert indicator that provides an alert when the moisture detection circuit is in the second state;
at least one processor;
a memory coupled to the at least one processor;
a wireless interface coupled to the at least one processor;
dryness detection software residing in the memory and executed by the at least one processor, the dryness detection software receiving an indication from the moisture detection circuit when the moisture detection circuit is in the second state that indicates a lack of moisture;
dryness alert software residing in the memory and executed by the at least one processor, the dryness alert software receiving an indication from the dryness detection software when the moisture detection circuit is in the second state, and in response thereto, sending an electronic message via the wireless interface to an electronic device external to the dryness sensor;
at least one rechargeable battery; and
at least one solar cell coupled to the at last one rechargeable battery so the solar cell charges the at least one rechargeable battery from ambient light.

10. The dryness sensor of claim 9 wherein the alert comprises a visual indication.

11. The dryness sensor of claim 9 wherein the alert comprises an audio indication.

12. The dryness sensor of claim 9 wherein electronic device external to the dryness sensor comprises a mobile phone running a software app that receives the electronic message, and in response to the electronic message, provide a notification on the mobile phone.

13. A method for indicating dryness comprising:
providing a dryness sensor that comprises:
a moisture detection chamber comprising:
at least one opening between an external portion of the dryness sensor and the moisture detection chamber so liquid that contacts the external portion of the dryness sensor can pass into the moisture detection chamber;
at least one electronic component;
a block of superabsorbent polymer that increases in size when the block of superabsorbent polymer absorbs liquid and decreases in size as the block of superabsorbent polymer loses liquid, wherein the block of superabsorbent polymer has a first dimension that contacts the at least one electronic component when the block of superabsorbent polymer has a liquid content above a first threshold and has a second dimension that does not contact the at least one electronic component when the block of superabsorbent polymer has a liquid content less than a second threshold; and
a moisture detection circuit coupled to the at least one electronic component in the moisture detection chamber, the moisture detection circuit having a first state that indicates moisture when the block of superabsorbent polymer contacts the at least one electronic component and having a second state that indicates lack of moisture when the block of superabsorbent polymer does not contact the at least one electronic component;
placing the moisture detection sensor in a location to sense moisture;
adding moisture to the location so the moisture detection circuit is in the first state that indicates moisture;
detecting when the moisture detection circuit changes from the first state that indicates moistures to the second state that indicates a lack of moisture; and
in response to the moisture detection circuit changing from the first state to the second state, providing an alert that indicates the lack of moisture.

14. The method of claim 13 wherein the alert comprises a visual indication.

15. The method of claim 13 wherein the alert comprises an audio indication.

16. The method of claim 13 wherein the alert comprises sending an electronic message via a wireless interface to an electronic device external to the dryness sensor.

17. The method of claim 16 wherein electronic device external to the dryness sensor comprises a mobile phone running a software app that receives the electronic message, and in response to the electronic message, provide a notification on the mobile phone.

* * * * *